US006896889B2

(12) United States Patent
Chevalier et al.

(10) Patent No.: US 6,896,889 B2
(45) Date of Patent: May 24, 2005

(54) IMMEDIATE EFFECT ANTI-WRINKLE COMPOSITION, BASED ON AN AQUEOUS DISPERSION, OF AT LEAST ONE MINERAL FILLER

(75) Inventors: Veronique Chevalier, Villecresne (FR); Veronique Roger, Bagneux (FR); Guillaume Cassin, Villebon sur Yvette (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/116,049

(22) Filed: Apr. 5, 2002

(65) Prior Publication Data

US 2003/0007985 A1 Jan. 9, 2003

(30) Foreign Application Priority Data

Apr. 6, 2001 (FR) .............................. 01 04743

(51) Int. Cl.$^7$ ................................. A61K 7/48
(52) U.S. Cl. ..................... 424/401; 514/937; 514/938; 424/489
(58) Field of Search ................. 424/401, 489, 424/DIG. 5; 514/937, 938

(56) References Cited

U.S. PATENT DOCUMENTS

| 3,819,825 A | | 6/1974 | Goodwin |
| 4,777,041 A | | 10/1988 | Mercado |
| 5,560,916 A | * | 10/1996 | Koulbanis et al. .......... 424/401 |
| 5,702,714 A | | 12/1997 | Goss |

FOREIGN PATENT DOCUMENTS

| DE | WO 97/35558 | 10/1997 |
| FR | 2659551 | 9/1991 |
| JP | 62198608 | 9/1987 |
| WO | WO 00/73374 A1 | 12/2000 |

* cited by examiner

*Primary Examiner*—Jyothsna Venkat
(74) *Attorney, Agent, or Firm*—Oblon, Spivak, McClelland, Maier & Neustadt, P.C.

(57) ABSTRACT

The invention relates to a cosmetic composition having an immediate anti-wrinkle effect, containing an effective amount of at least one mineral filler, with the exclusion of any mixed silicate, the mineral filler being in the form of colloid particles in a stable dispersion in an aqueous medium. The invention also relates to using such a filler as a tensing agent in and/or for preparing a cosmetic composition.

43 Claims, No Drawings

IMMEDIATE EFFECT ANTI-WRINKLE COMPOSITION, BASED ON AN AQUEOUS DISPERSION, OF AT LEAST ONE MINERAL FILLER

FIELD OF THE INVENTION

The invention relates to a composition having an immediate anti-wrinkle effect and containing, in a physiologically acceptable aqueous medium, an effective amount of at least one mineral filler in the form of colloid particles in a dispersion in an aqueous medium.

The present invention also relates to using in and/or to preparing a composition comprising at least one mineral filler as a tensing agent in order to tense the skin and to smooth the same in order to immediately attenuate the wrinkles and/or the fine wrinkles.

BACKGROUND OF THE INVENTION

In the aging process, various signs appear on the skin resulting from a modification of skin structure and of cutaneous function. The main clinical signs of aging are, among others, the appearance of fine wrinkles and deep wrinkles. These signs of aging increase with age. A disorganization of skin "texture" is more particularly observed, meaning that micro-contours are less regular and show an anisotropic character.

It is known to treat these signs of aging using cosmetic or dermatological compositions containing actives adapted to fight against such signs of aging, such as α-hydroxy-acids, β-hydroxy-acids and retinoids. Such actives act on wrinkles primarily by eliminating dead skin cells and accelerating the cell renewal process.

However, the visible effect of such compositions is generally observed after some application time, ranging from a few days to several weeks.

Several compositions have been suggested which have a tensing effect, making it possible to obtain an immediate skin smoothing.

Such compositions generally contain as a tensing agent substances from natural origin, such as plant, egg, milk or animal derivatives. For instance, the International Application WO-98/29091 discloses the use, as a tensing agent, of a polymeric system having particular physico-chemical properties and comprising at least one polymer from natural origin, such as a soya protein extract or chitin or keratin derivatives. Moreover, the International Application WO 96/19180 discloses toning compositions comprising a film-forming agent containing at least one plant polysaccharide and hydrolyzed casein as tensing actives. However, the use of substances from natural origin is limited by hazards associated with bovine spongiform encephalopathy. Moreover, not only are tensing effects not always reproducible, but the tensing effect obtained from such substances is not very significant from a qualitative standpoint, and from a quantitative standpoint, the effect shows a low remanence.

Other prior art compositions having a tensing effect use synthetic polymers. PCT Application WO-98/29022 discloses a composition having a tensing effect and comprising an aqueous dispersion of a polymeric system containing at least one polymer from plastic origin selected from the group comprising several types of polyurethanes, polyureas, acrylic polymers or copolymers, sulfonated isophthalic acid polymers and the mixtures thereof. The cosmetic feel of such compositions is, however, not satisfactory.

Additionally, European Patent Application EP-1038519-A1 discloses the use as a tensing agent in and/or for the manufacture of an anti-wrinkle composition, of at least one grafted silicone polymer comprising one polysiloxane portion and one portion consisting of a non silicone organic chain, one of the two portions constituting the main chain and the other one being grafted on said main chain. However, such silicone polymers do not exhibit satisfactory anti-wrinkle effects when they are formulated in an emulsion.

The use of mineral fillers and more particularly of silica in cosmetic compositions is known. For instance, silica is a widely used material in the cosmetic industry. It confers softness and a matte aspect to the formulations. It is also used in association with titanium dioxide or zinc oxide for forming complex particles with sun filter effects. For such applications, silica is very often in pulverulent form and a wide range of particle sizes is available from 1 $\mu$m to 100 $\mu$m. However it is far less usual, and even exceptional, to use colloid particles.

European Patent Application EP-1 008 334-A2 discloses the use and preparation, at an acidic pH, of mixed silicates, as tensing agents, for tensing and smoothing the skin, in order to immediately attenuate the skin wrinkles and/or fine wrinkles, the mixed silicates being in the form of particles having an average size ranging from 15 to 1000 nm resulting in colloid solutions. However, nothing is mentioned regarding fillers other than mixed silicates. Moreover, the tensing effect and the smoothing power are attributed to the chemical nature of the mixed silicates and not to the particle size.

Accordingly, there remains a need for compounds offering an immediate tensing effect, which are satisfactory and durable, which do not pose any risk for the consumer and are able to be formulated in compositions comprising fatty phases. The present invention precisely aims at meeting such a need.

SUMMARY OF THE INVENTION

Applicant has surprisingly discovered that the use of mineral fillers in a composition provides such a composition, after application onto the skin, with an excellent instantaneous smoothing effect of the skin surface layer when such fillers are in the form of colloid particles in a stable dispersion in an aqueous medium. Such fillers in the form of colloid particles can therefore be used as tensing agents in immediate effect anti-wrinkle compositions.

The present invention provides compositions having an immediate anti-wrinkle effect, containing, in a physiologically acceptable medium, an effective amount of at least one mineral filler, with the exclusion of any mixed silicate, characterized in that the mineral filler is in the form of colloid particles so that at least 70% of them have a diameter in the range from 0.1 to 100 nm, preferably from 3 to 30 nm, in a dispersion in an aqueous, alcoholic or hydroalcoholic medium.

DETAILED DESCRIPTION OF THE INVENTION

As used herein, "tensing agent" means a compound able to have an apparent tensing effect, i.e., able to smooth the skin and to reduce or attenuate, even to make disappear, immediately, wrinkles and fine wrinkles.

As used herein, "colloid particles" means particles with a size on the order of ten nanometers or so.

As used herein, "physiologically acceptable medium" means a non-toxic medium adapted to be applied onto the skin (as well as inside the eye-lids) or onto the human being lips.

As used herein, "aqueous medium" means a medium containing only water as well as a medium containing water and a hydrosoluble solvent such as a lower alcohol comprising 1 to 6 carbon atoms or a glycol.

As used herein, "effective" or "efficient" amount means a sufficient amount for reaching the aimed objective, i.e., an instantaneous tensing and smoothness effect. Such an amount depends on the dispersion of the mineral filler being used and of other composition compounds.

As used herein, "diameter" means the number average diameter.

The granulometry is determined using a Particle size analyser 90 granulometer, available from Brookhaven Instrument Corporation.

In accordance with the present invention, colloid particles are generally present in the composition in an active material amount ranging from about 0.5 to about 15% wt, and preferably from about 3 to about 10% wt based on the total weight of the composition. These ranges include all numerals and fractions thereof including 1, 2, 3, 4, 5, 6, 7, 8, 9 10, 11, 12, 13, and 14 wt based on the total weight of the composition.

The mineral filler colloid particles suitable for use in the present invention are preferably non-gelling.

As used herein, "non-gelling particles" means that a concentration greater than or equal to 15% wt based on the total weight of the composition, in an aqueous, alcoholic or hydroalcoholic medium, the viscosity of colloid particle solutions in said medium is lower than 0.05 Pa.s for a $10\,s^{-1}$ shear rate, the measure being taken at 25° C. using a Rheostress RS150 Rheometer available from Haake in a cone-plane, configuration, the measure cone having a 60 nm diameter and a 2° angle.

The mineral filler colloid particles suitable for use in the present invention are generally selected from silica, cerium oxide, zirconium oxide, alumina, calcium carbonate, barium sulfate, calcium sulfate, zinc oxide and titanium dioxide colloid particles, platinum colloid particles, mixed colloid particles, such as, for instance, once or several coated titanium dioxides, such as silica coated titanium dioxide.

Colloid silicas are preferred. As used herein, "colloid silicas" means silica colloid particles being dispersed in an aqueous, hydroalcoholic, alcoholic medium. Colloid silicas usable in the composition according to the invention include, for instance, those commercialized by Catalysts and Chemicals Company, under the designations Cosmo S-40 and Cosmo S-50.

The composition according to the invention may comprise only an aqueous phase, in that case in the form of serum or gel, for example.

The composition according to the invention may also comprise an oil phase containing at least one oil.

Oils usable in the composition of the invention may include for example:

hydrocarbon oils from animal origin, such as perhydrosqualene;

hydrocarbon oils from plant origin, such as liquid fatty acid triglycerides comprising from 4 to 10 carbon atoms such as heptanoic or octanoic acid triglycerides or, additionally, sun-flower, maize, soya, marrow, grape seeds, sesame, hazelnut, apricot, macadamia, arara, avocado and castor oils, caprylic/capric acid triglycerides, such as those sold by Stearineries Dubois company or those sold under the designations Miglyol 810, 812 and 818 by Dynamit Nobel company, jojoba oil, shea butter oil;

synthesis esters and ethers, including from fatty acids, such as oils with the formulas $R^1COOR^2$ and $R^1OR^2$ wherein $R^1$ represents the moiety of a fatty acid comprising 8 to 29 carbon atoms, and $R^2$ represents a branched or unbranched hydrocarbon chain, containing from 3 to 30 carbon atoms, such as, for instance, Purcellin oil, isononyl isononanoate, isopropyl myristate, ethyl-2-hexyl palmitate, octyl-2-dodecyl stearate, octyl-2-dodecyl erucate, isostearyl isostearate; hydroxyl esters such as isostearyl lactate, octyl hydroxystearate, octyldodecyl hydroxystearate, diisocstearyl malate, triisocetyl citrate, fatty alcohol heptanoates, octanoates and decanoates; polyol esters such as propylene glycol dioctanoate, neopentyl glycol diheptanoate and diethylene glycol diisononanoate; and pentaerythritol esters such as pentaerythrityl tetraisostearate;

straight or branched hydrocarbons, from mineral or synthetic origin, such as volatile or not volatile paraffin oils and their derivatives, vaseline, polydecenes, hydrogenated polyisobutene, such as Parleam™ (sold by Nippon Gel Fats Company);

fatty alcohols with from 8 to 26 carbon atoms, such as cetyl alcohol, stearyl alcohol and the mixtures thereof (cetylstearyl alcohol), octyldodecanol, 2-butyloctanol, 2-hexyldecanol, 2-undecylpentadecanol, oleic alcohol or linoleic alcohol;

alkyl fatty alcohols, including ethoxylated, such as oleth-12;

partially hydrocarbon and/or silicon fluorinated oils, such as those described in document JP-A-2-295912. Fluorinated oils may also include perfluoromethylcyclopentane and perfluoro-1,3 dimethylcyclohexane, sold under trademarks FLUTEC PC 1™ and FLUTEC PC3™ by BNFL Fluorochemicals company; perfluoro-1,2-dimethylcyclobutane; perfluoroalkanes such as dodecafluoropentane and tetradecafluorohexane sold under trademarks PF 5050™ and PF $_{5060}$™ by 3M Company or also bromoperfluorooctyl sold under trademark FORALKYL™ by Atochem company; nonafluoromethoxybutane sold under trademark MSX 4518™ by 3M company and nonafluoroethoxyisobutane; perfluoromorpholine derivatives, such as 4-trifluoromethyl perfluoromorpholine sold under trademark PF-5052™ by 3M company; silicone oils such as polymethylsiloxanes (PDMS), either volatile or not, with a straight or cyclic silicone chain, liquid or pasty at room temperature, including cyclopolydimethylsiloxanes (cyclomethicones) such as cyclohexasiloxane; polydimethylsiloxanes comprising alkyl, alkoxy or phenyl groups, either pendant or at silicone chain end, having from 2 to 24 carbon atoms; phenylated silicones such as phenyltrimethicones, phenyldimethicones, phenyltrimethylsiloxydiphenylsiloxanes, diphenyldimethicones, diphenylmethyldiphenyl trisiloxanes, 2-phenylethyltrimethylsiloxysilicates, and polymethylphenyl-siloxanes; and mixtures thereof.

As used herein, "hydrocarbonated oil" means any oil having mainly carbon and hydrocarbon atoms and, optionally, ester, ether, fluorinated, carboxylic acid and/or alcohol groups.

The oil phase may also comprise other fatty substances, such as fatty acids having from 8 to 30 carbon atoms, such as stearic acid, lauric acid, palmitic acid and oleic acid; natural waxes such as lanolin, beewax, Carnauba or Candelilla wax, paraffin waxes, lignite waxes, or microcrystalline waxes, ceresine or ozokerite, synthetic waxes such as polyethylene waxes, Fischer-Tropsch waxes; gums such as silicone gums (dimethiconol); silicone resins such as trifluoromethyl-$C_{1-4}$-alkyldimethicone and trifluoropropyldimethicone; and silicone elastomers such as the products sold under trademark KSG™ by Shin-Etsu company, under trademarks Trefil™, BY29™ or EPSX™ by Dow Coming company or under trademark Gransil™ by Grant Industries company.

Such fatty substances may be selected, on a variable basis, by one skilled in the art for preparing such a composition having, for example, the desired consistency or texture properties.

The composition pH preferably ranges from about 5 to about 8, more preferably from about 6 to about 7. It can be adjusted by adding acid, such as, for example, hydrochloric acid or citric acid.

The compositions according to the invention may be in all the galenic forms conventionally used for a topic application, including in the form of aqueous, hydroalcoholic or oily solutions, oil-in-water emulsions (O/W), or water-in-oil emulsions (W/O), or multiple emulsions, such as water-in-oil-in-water emulsions (W/O/W) of aqueous or oily gels, of liquid anhydrous products, either pasty or solid, or dispersions of a greasy phase in an aqueous phase in the presence of spherules, such as spherules being adapted to be polymeric nanoparticles such as nanospheres or nanocapsules, or lipidic vesicles, either of a ionic and/or non ionic type. Such compositions are prepared according to the usual methods.

Moreover, compositions used according to the invention can be more or less fluid and show the aspect of a white or coloured cream, a balm, a milk, a lotion, a serum, a paste or a foam.

They may possibly be applied onto the skin in the form of an aerosol. They may also be in a solid form, such as a stick.

According to a particular embodiment of the invention, the composition according to the invention is a water-in-oil (W/O) or oil-in-water (O/W) or water-in-oil-in-water (W/O/W) emulsion. Such a composition is preferably free from low molecular weight polyol, i.e., $C_1$–$C_5$. Such polyols are in particular glycerin and propylene glycol.

The oil phase proportion in the emulsion may range from about 5 to about 80% wt, and more preferably from about 5 to about 50% wt based on the total weight of the composition.

Oils, emulsifiers and co-emulsifiers used in the composition in the form of an emulsion are selected from those conventionally used in the cosmetic or dermatological field. The emulsifier and co-emulsifier are generally present in the composition in a proportion ranging from about 0.3 to about 30% wt, and preferably from about 0.5 to about 20% wt, based on the total weight of the composition. The emulsion can additionally contain lipidic vesicles.

The emulsions generally contain at least one emulsifier selected amongst amphoteric, anionic, cationic or non ionic emulsifiers, being used alone or in blends. The emulsifiers are appropriately selected depending on the emulsion to be obtained (W/O or O/W).

The emulsions can also contain emulsifying surfactants.

Emulsifying surfactants usable for preparing W/O emulsions may include, for example, sorbitan, glycerol or sugar alkyl esters or ethers; silicone surfactants such as dimethicone copolyols like cyclomethicone and dimethicone copolyol blend, sold under trademarks DC 5225 C™ or DC 3225C™ by Dow Coming company, and alkyl-dimethicone copolyol such as Laurylmethicone copoly sold under trademark Dow Corning 5200 Formulation Aid™ by Dow Corning company and cetyl dimethicone copolyol sold under trademark Abil EM 90™ by Goldschmidt company.

O/W emulsions may include, for example, as emulsifiers, non ionic emulsifiers, such as oxyalkylinated (more particularly polyoxyethylenated) fatty acid glycerol esters; oxyalkylenated fatty acid sorbitan esters; oxyalkylenated (oxyethylenated and/or oxypropylenated) fatty acid esters; oxyalkylenated (oxyethylenated and/or oxypropylenated) fatty alcohol ethers; sugar esters such as sucrose stearate. One can mention, among others, the dimyristyl tartarate/cetearly alcohol/$C_{12-15}$ Pareth-7/PPG-25 Laureth-25 blend (name CFTA) sold under trademark COSMACOL PSA™ by CONDEA company.

It is known that the cosmetic or dermatological composition of the invention may also contain usual adjuvants in the cosmetic or dermatological field, such as hydrophilic or lipophilic gelling agents, hydrophilic or lipophilic actives, preservatives, antioxidants, solvents, perfumes, fillers, lipophilic or hydrophilic sun filters, bactericides, odour absorbents, clourants, salts and polymers. The amounts of these various adjuvants are those conventionally used in the involved field and, for example, range from about 0.01 to about 30% of the total weight of the composition. Such adjuvants, according to their nature, can be introduced into the greasy phase, in the aqueous phase and/or in the lipidic spherules.

Fillers adapted to be used in the composition of the invention may include, for example, besides pigments, fibres; talcum; polyamide particles, more particularly those sold under trademark ORGASOL™ by Atochem company; polyethylene powders; acrylic copolymer based microspheres, such as those made of a copolymer of ethylene glycol dimethacrylate and lauryl methacrylate, sold by Dow Corning company under trademark POLYTRAP™; expanded powders such as hollow microspheres and, more particularly, microspheres sold under trademark EXPANCEL™ by Kemanord Plast company or under trademark MICROPEARL F 80 ED™ by Matsumoto company; powders from natural organic materials such as maize, wheat or rice starches, either cross-linked or not, such as the starch powders cross-linked by the octenylsuccinate anhydride sold under trademark DRY-FLO™ by National Starch company; silicone resin microballs such as those sold under trademark TOSPEARL™ by Toshiba Silicone company; and mixtures thereof. Such fillers may be present in amounts ranging from 0 to 20% wt, and preferably, from 1 to 10% wt based on the total weight of the composition.

Hydrophilic gelling agents may include, for example, carboxyvinyl polymers such as products sold under trademark CARBOPOL™ (CTFA name: carbomer) by Goodrich company, acrylic copolymers such as acrylate/alkylacrylate copolymers, polyacrylamides, and, for example, the mixture sold under tradename SEPIGEL™, 2-acrylamido 2-methylpropane sulfonic acid polymers and copolymers, either cross-linked or not, and neutralized or not, such as the product sold by Hoechst company under trademark "Hostacerin AMPS" (CTFA name: ammonium polyacryldimethyltauramide), polysaccharides such as cellulose derivatives, and more particularly hydroxyethylcellulose, natural gums such as xanthane gum, and clays.

Lipophilic gelling agents may include the modified clays such as bentones, fatty acid metal salts, polymers and copolymers of vinyl methyl ether and maleic anhydride such as products sold under trademarks STABILEZE™ by ISP company (CTFA name: PVM/MA Decadiene Crosspolymer), and polyethylenes.

Actives may include in particular all the actives known for their activity on skin ageing, such as keratolytic or prodesquamant agents, for example, α-hydroxy-acids, such as glycolic, lactic, malic, citric, tartaric, mandelic acids and the derivatives thereof; β-hydroxy-acids such as salicylic acid and the derivatives thereof; α-aceto-acids such as ascorbic acid or vitamin C and the derivatives thereof; β-ceto-acids; retinoids such as retinol (vitamin A) and the esters thereof (palmitate), retinal, retinoic acid and the derivatives thereof.

Actives may also include vitamins, such as, for example, vitamins B3 or PP (niacinamide), B5 (panthénol), E (tocopherol), K1 and the derivatives of those vitamins and more particularly the esters thereof; anti-free radical agents; sun filters; hydrating agents such as polyols; ceramides; and tensing polymers including organics such as latexes, protein hydrolysates and chitin derivatives; DHEA and the derivatives thereof such as alpha-hydroxy-DHEA; Q10 coenzyme, bleaching and depigmenting agents, such as kojic acid para-aminophenol derivatives, arbutin and the derivatives thereof, and the blends thereof.

As chemical sun filters useful in the composition of the invention, the composition of the invention may comprise every UVA and UVB filter useful in the cosmetic field.

UVB filters may include for example:
1. salicylic acid derivatives, more particularly homomenthyl salicylate and octyl salicylate;
2. cinnamic acid derivatives, more particularly 2-ethylhexyl p-methoxycinnamate sold by Givaudan company under trademark PARSOL MCX™;
3. liquid (β'-β-diphenylacrylate) derivatives, more particularly 2-ethylhexyl α-cyano-α-β-diphenylacrylate or octocrylene sold by BASF company under trademark UVINUL N539™;
4. p-aminobenzoic acid derivatives;
5. 4-methyl benzylidene camphor sold by Merck company under trademark EUSOLEX 6300™;
6. 2-phenylbenzimidazole 5-sulfonic acid sold under trademark EUSOLEX 232™ by Merck company;
7. 1,3,5-triazine derivatives, more particularly:
   2,4,6-tris[p-2'-ethylhexyl-1'-oxycarbonyl)anilino]-1,3,5-triazine sold by BASF company under trademark UVINUL $T_{150}$™, and
   dioctyl butamido triazone sold by Sigma 3V company under trademark UVASORB HEB™, and
8. mixtures of such filter.

UVA filters may include for example:
1. dibenzoylmethane derivatives, more particularly 4-(tert-butyl)4'-methoxy dibenzoylmethane sold by Givaudan company under trademark PARSOL 1789™;
2. benzene 1,4[di(3-methylidenecampho-10-sulfonic)] acid, possibly under a partially or totally neutralized form, sold under trademark MEXORYL SX™ by Chimex company;
3. benzophenone derivatives, for example:
   2,4 dihydroxybenzophenone (benzophenone-1),
   2,2',4,4'-tetra-hydroxybenzophenone (benzophenone-2),
   2-hydroxy-4-methoxy-benzophenone (benzophenone-3) sold under trademark UVINUL M40™ by BASF company,
   2-hydroxy-4-methoxy-benzophenone-5-sulfonic acid (benzophenone-4) as well as the sulfonate form thereof (benzophenone-5) sold by BASF company under trademark UVINUL MS40™,
   2,2'-dihydroxy-4,4'-dimethoxy-benzophenone (benzophenone-6),
   5-chloro-2-hydroxybenzophenone (benzophenone-7),
   2,2'-dihydroxy-4-methoxy-benzophenone (benzophenone-8),
   the disodium salt of the 2,2'-dihydroxy-4,4-dimethoxybenzophenone-5,5'-disulfonic diacid (benzophenone-9),
   2-hydroxy-4-methoxy-4'-methyl-benzophenone (benzophénone-10),
   benzophenone-11,
   2-hydroxy-4-(octyloxy)enzophenone (benzophenone-12);
4. silane derivatives or polyorganosiloxanes with a benzophenone group;
5. anthranilates, more particularly the menthyl anthranilate sold by Haarman & Reiner company under trademark NEO HELIOPAN MA™;
6. compounds having per molecule at least two benzoazolyl groups or at least one benzodiazolyl group, more particularly the 14-bis-benzimidazolyl-phenylene-3,3', 5,5'-tetrasulfonic acid as well as the salts thereof sold by Haarman & Reiner company;
7. silica-based derivatives of N-substituted benzimidazolyl-benzazoles or benzofuranyl-benzazoles, and in particular:
   2-[1-[3-[1,3,3,3-tetramethyl-1-[(trimethylsilyl)oxy]-disiloxanyl]-propyl]-1H-benzimidazol-2-yl]-benzoxazole,
   2-[1-[3-[,3,3,3-tetramethyl-1-[(trimethylsilyl)oxy]-disiloxanyl]-propyl]-1H-benzimidazol-2-yl]-benzoxazole,
   2-[1-(3-trimethylsilanyl-propyl)-1H-benzimidazol-2-yl]-benzoxazole,
   6-methoxyl-1,1'-bis(3-trimethylsilanyl-propyl)-1H, 1'H-[2,2']bibenzimidazolyl-benzoxazole,
   2-[1-(3-trimethylsilanyl-propyl)-1H-benzimidazol-2-yl]-benzothiazole, which are described in Patent Application EP-A-1 028 120;
9. triazine derivatives, and more particularly, the 2,4-bis{[4-(2-ethyl-hexyloxy)-2-hydroxy]-phenyl}-6-(4-phenyl)-1,3,5-triazine sold by Ciba Geigy compnay under trademark TINOSORB S™ and the 2,2'-methylenebis-[6-(2H benzotriazol-2-yl)4-(1,1,3,3-tetramethylbutyl)-phenol] sold by Ciba Geigy company under trademark TINOSORB M™;
10. the mixtures thereof.

A blend of several of such filters may also be used, as well as a blend of UVB and UVA filters, and also blends with physical filters.

Physical filters may include titanium (amorphous or crystallized titanium dioxide under the rutile or anatase form), zinc, iron, zirconium, cerium oxides or the blends thereof. Such metal oxides can be in the form of particles having a micrometric or a nanometric size (nano-pigments). In the nano-pigment form, the particle average sizes range, for example, from about 5 to about 100 nm. Nano-pigments are preferably used in the composition of the invention.

Filters usually used in the composition of the invention include preferably 2-ethylhexyl p-methoxycinnamate sold under trademark Parsol MCX by Hoffmann-Laroche company, benzene 1,4[di(3-methylidenecaampho-10-sulfonic )] acid sold under trademark MEXORYL SX™ by Chimex company, 2-hydroxy-4-methoxy-benzophenone sold under trademark UVINUL M40™ by BASF company, 2-phenylbenzimidazole-5 sulfonic acid sold under trademark EUSOLEX 232™ by Merck company, and the blends thereof.

The active amount depends on the desired final use. It can range for example from about 0.001 to about 30% wt, preferably from about 0.05 to about 20% wt and more preferably from about 0.5 to about 15% wt based on the total weight of the composition.

The invention allows for skin smoothing and skin wrinkle and fine wrinkle attenuation.

The invention therefore also provides a cosmetic treatment method for tensing and smoothing the skin for immediately attenuating the wrinkles and/or the fine wrinkles, characterized in that a composition such as defined here above is applied onto the skin.

The invention also aims at a cosmetic treatment method for a wrinkled skin, wherein a composition such as defined here above is applied onto said wrinkled skin, in an effective amount for immediately attenuating wrinkles or fine wrinkles by a tensing effect.

The invention also aims at using an effective amount of at least one mineral filler, such as defined here above as a tensing agent in and/or for preparing a cosmetic composition.

The invention will be illustrated using the following non limitative examples. The amounts are indicted in % wt unless otherwise specified.

EXAMPLES

Example 1

O/W Emulsion

A O/W emulsion is prepared from ingredients in Table 1.

TABLE 1

| | CTFA names | Amount (% wt) |
|---|---|---|
| Phase A | Dimyristyl tartarate/cetearyl alcohol/$C_{12}$–$C_{15}$ Pareth-7/PPG-25 Laureth-25 | 1.5 |
| | Stearyl alcohol | 1 |
| | Oils | 10 |
| | Preservative | 0.15 |
| | Ethylhexyl methoxycinnamate | 1 |
| Phase B | Glycerin | 5 |
| | Preservatives | 0.5 |
| | Disodium EDTA | 0.05 |
| | Ammonium polyacryl dimethyltauride (AMPS Hostacerin(™)) | 0.4 |
| | Water | qsp 100% |
| Phase C | Xanthan gum | 0.2 |
| Phase D | Silica (COSMO S-40(™)) | 17.5 |

Operating Mode:

Phase B is heated at about 75° C. and AMPS Hostacerin™ is incorporated therein, stirring is carried out until a homogenous gel is obtained.

then phase A is heated at about 75° C., the emulsion is prepared under stirring by incorporating phase A into phase B, and then phase C is added still under stirring, and afterwards, phase D is incorporated at a temperature ranging from 40 to 45° C. and stirring is maintained until complete cooling.

Example 2

Anti-ageing Serum

An anti-ageing serum is prepared from ingredients as indicated in Table 2.

TABLE 2

| | CTFA names | Amount (% wt) |
|---|---|---|
| Phase A | Xanthan gum | 0.2% |
| | PVM/MA Decadiene crosspolymer | 0.2% |
| | Preservatives | qs |
| | Water | qsp 100% |
| Phase B | Triethanolamine | 0.2% |
| Phase C | Polyacrylamide, $C_{13}$–$C_{14}$ isoparaffin and Laureth-7 (SEPIGEL 305(™)) | 1% |
| Phase D | Silica (Cosmo S-40(™)) | 17.5% |

Operating Mode:

Phase A is heated at about 75° C. and xanthan gum and the PVM/MA decadiene crosspolymer are dispersed under stirring, then phase B is added under stirring at 40° C., phase C is added, and afterwards, phase D is incorporated and stirring is maintained until complete cooling.

The anti-wrinkle character is emphasized as follows:

on human models: pictures of the models are taken before any product is applied, and subsequently, after applying an emulsion containing 7% (in active material) colloid silica, and the pictures are compared. A net reduction of the wrinkle visibility can be observed (particularly crow's-foot and under the eyes), by measurement with an extensometer: the retraction percentage of the stratum corneum specimen reaches– 1.3+/–0.,5 for cream from Example 1 and –2.2%/0.4 for serum from Example 2.

Evaluation of the Tensing Effect by Measurement with an Extensometer

The method principle comprises the step of measuring the length of a stratum corneum specimen isolated from a human skin obtained from a surgical operation, before and after treatment with the compositions to be tested.

To do this, the specimen is placed between the two jaws of the apparatus, one of which is fixed and the other is moveable, in a 30° C. atmosphere and with a 40% relative humidity.

Some pull-out is exerted on the specimen and the force curve (in grammes) is recorded as a function of the length (in millimeters), a zero length corresponding to the contract between the two jaws of the apparatus.

Afterwards, the tangent to the curve is plotted in the linear area. The intersection of said tangent with the abscissa axis corresponds to the apparent length L0. of the specimen at nil force.

The specimen is released and 2 mg/cm² of the composition to be tested are applied on the stratum corneum. After drying for 15 minutes, the above-mentioned steps are repeated to determine the L1 length of the specimen after treatment.

The retraction percentage is defined as follows:

% retraction=100×(L1–L0.)/L0.

To characterize a tensing effect, such percentage should be negative and the tensing effect is all the more higher as the absolute value of the retraction percentage is higher.

Example 3

Anti-wrinkle cream and serums: influence of glycerin absence

Two anti-wrinkle creams C1 and C2 have been prepared, each containing 15% colloid silica, from the ingredients indicated in Table 3, the cream C1 containing 5% wt glycerin based on the total weight o from it.

Two anti-wrinkle serums, S1 and S2, have also been prepared, each also containing 15% colloid silica, from the ingredients indicated in Table 4, the serum S1 containing 5% wt glycerin and the serum S2 being free from it.

TABLE 3

| | CTFA names | Cream C1 (% wt) | Cream C2 (% wt) |
|---|---|---|---|
| Phase A | Dimyristyl tartarate/cetearyl alcohol $C_{12}$—$C_{15}$ Pareth-7/PPG-25 Laureth-25 | 1.5 | 1.5 |
| | Stearyl alcohol | 1 | 1 |
| | Oils | 10 | 10 |
| | Preservative | 0.15 | 0.15 |
| | Ethylhexyl methoxy cinnamate | 1 | 1 |
| Phase B | Glycerin | 5 | 0 |
| | Preservatives | 0.5 | 0.5 |
| | Diosodium EDTA | 0.05 | 0.05 |
| | Ammonium polyacryl dimethyltauride (AMPS Hostacerin(™)) | 0.4 | 0.4 |
| | Water | qsp 100% | qsp 100% |
| Phase C | Xanthan gum | 0.2 | 0.8 |
| Phase D | Silica (COSMO S-40(™)) | 15 | 15 |

TABLE 4

| | CTFA names | Serum S1 (% wt) | Serum S2 (% wt) |
|---|---|---|---|
| Phase A | Xanthan gum | 0.2 | 0.2 |
| | Glycerine | 5 | 0 |
| | PVM/MA Decadiene crosspolymer | 0.2 | 0.2 |
| | Preservatives | qs | qs |
| | Water | qsp 100 | qsp 100 |
| Phase B | Triethanolamine | 0.2 | 0.2 |
| Phase C | Polyacrylamide, $C_{13}$—$C_{14}$ isoparaffin and Laureth-7 (SPIEGEL 305(™)) | 1 | 1 |
| Phase D | Silica (COSMO S-40(™)) | 15 | 15 |

The immediate anti-wrinkle character is emphasized through a measurement with an extensometer of the retraction percentage of an isolated stratum corneum specimen, in the same way as in Example 2.

The results of these measurements are presented in Table 5.

TABLE 5

| Compositions | % retraction of a isolated stratum corneum specimen |
|---|---|
| Cream C1 (with glycerin) | −1.15+/−0.21 |
| Cream C2 (without glycerin) | −2.16+/−0.42 |
| Serum S1 (with glycerin) | −1.08+/−0.35 |
| Serum S2 (without glycerin) | −2.50+/−0.35 |

These results show that the tensing power of the cosmetic compositions containing mineral filler colloid particles and glycerin is lower than that of identical compositions, but with no glycerin.

This application claims priority from French Patent Application No. 0104743 filed Apr. 6, 2001, the entire disclosure of which is incorporated by reference.

What is claimed is:

1. A composition having an immediate anti-wrinkle effect comprising in a physiologically acceptable medium, an anti-wrinkle effective amount of at least one mineral filler, with the exclusion of any mixed silicate, wherein the composition is in the form of an emulsion comprising at least one oil phase, wherein the mineral filler is in the form of colloid particles in a dispersion in an aqueous, alcoholic or hydroalcoholic medium and wherein at least 70% of the particles have a diameter in the range of about 0.1 to about 100 nm.

2. A composition according to claim 1, wherein at least 70% of the colloid particles have a diameter in the range from about 3 to about 30 nm.

3. A composition according to claim 1, wherein the colloid particles are present in the composition in an active material amount ranging from about 0.5 to about 15% wt based on the total weight of the composition.

4. A composition according to claim 1, wherein the colloid particles are present in the composition in an active material amount ranging from about 3 to about 10% wt based an the total weight of the composition.

5. A composition according to claim 1, wherein the mineral filler colloid particles are selected from the group consisting of silica, cerium oxide, ziconium oxide, alumina, calcium carbonate, barium sulfate, calcium sulfate, zinc oxide, titanium dioxide colloid particles, platinum colloid particles, zinc oxide colloid particles and mixed colloid particles.

6. A composition according to claim 5, wherein the colloid particles are silica.

7. A composition according to claim 1, wherein the at least one oil phase comprises at least one oil selected from the group consisting of hydrocarbon oils from plant origin, hydrocarbon oils from animal origin, partially hydrocarbon and/or silicone fluorinated oils, silicone oils, linear or branched hydrocarbons from mineral or synthetic origin, fatty alcohols having 8 to 26 carbon atoms, alkylated fatly alcohols and ethoxylated fatty alcohols.

8. A composition according to claim 7, wherein the at least one oil phase further comprises at least one fatty substance selected from the group consisting of fatty acids having 8 to 30 carbon atoms, natural waxes, synthetic waxes, gums and silicone elastomers.

9. A composition according to claim 1, wherein the composition has a pH ranging from about 5 to about 8.

10. A composition according to claim 1, wherein the composition has a pH ranging from about 6 to about 7.

11. A composition according to claim 1, wherein the composition is in a form selected from the group consisting of an oil-in-water emulsion (O/W) and a water-in-oil emulsion (W/O).

12. A composition according to claim 1, wherein the composition is a cream, a lotion, a paste, or a stick.

13. A composition according to claim 1, wherein the composition is in the form of a water-in-oil-in-water (W/O/W) emulsion.

14. A composition according to claim 1, wherein the composition is free from glycerin and propylene glycol.

15. A composition according to claim 1, wherein the at least one oil phase represents from 5 to 80% wt based on the total weight of the composition.

16. A composition according to claim 1, wherein the at least one oil phase represents from 5 to 50% wt based on the total weight of the composition.

17. A composition according to claim 13, wherein the composition comprises at least one emulsifier selected from the group consisting of amphoteric, anionic, cationic, and non-ionic emulsifiers, and mixtures thereof.

18. A composition according to claim 1, wherein the composition contains one or more adjuvants selected from the group consisting of hydrophilic or lipophilic gelling agents, hydrophilic or lipophilic active agents, preservatives, antioxidants, solvents, perfumes, fillers, lipophilic or hydrophilic sun filters, bactericides, odor absorbents, colorants, salts, and polymers.

19. A composition according to claim 18, wherein the adjuvant is present in the range from about 0.01 to about 30% wt based on the total weight of the composition.

20. A composition according to claim 18, wherein the hydrophilic gelling agent is selected from the group consisting of carboxyvinyl polymers, acrylic copolymers, polyacrylamides, 2-acrylamido-2-methylpropane sulfonic acid polymers and copolymers, polysaccharides and natural gums.

21. A composition according to claim 18, wherein the lipophilic gelling agent is selected from the group consisting of modified clays, fatty acid metallic salts, vinyl methyl ether and maleic anhydride polymers and copolymers, and polyethylenes.

22. A composition according to claim 18, wherein the active agent is selected from the group consisting of anti-aging agents, vitamins B3, B5, E and K, anti-free radical agents, sun filters, hydrating agents, ceramides, tensing polymers, DHEA, Q10 coenzyme, bleaching agents, and depigmenting agents.

23. A composition according to claim 22, wherein the anti-aging agent is selected from the group consisting of keratolytic agents, α-hydroxy-acids, α-keto-acids, β-keto-acids and retinoids.

24. A composition according to claim 22, wherein the active agent is present in a range from about 0.05 to about 20% wt based on the total weight of the composition.

25. A composition according to claim 22, wherein the active agent is present in a range from about 0.001 to about 30% wt based on the total weight of the composition.

26. A composition according to claim 22, wherein the active agent is present in a range from about 0.5 to about 15% wt based on the total weight of the composition.

27. A composition according to claim 18, wherein the filler is selected from the group consisting of pigments, fibres, talcum, polyamide particles, acrylic copolymer based microspheres, expanded powders, powders from natural organic materials and silicone resin microballs.

28. A composition according to claim 27, wherein the filler is present in a range from about 0 to about 20% wt based on the total weight of the composition.

29. A composition according to claim 27, wherein the filler is present in a range from about 1 to about 10% wt based on the total weight of the composition.

30. A composition according to claim 22, wherein the sun filter is selected from the group consisting of UVA filters, UVB filters, physical filters and mixtures thereof.

31. A method of immediately attenuating wrinkles and/or fine wrinkles comprising applying to skin a wrinkle or fine line attenuating effective amount of the composition according to claim 1.

32. A method for treating wrinkled skin comprising applying to the skin a wrinkle treating effective amount of the composition according to claim 1.

33. A method of tensing and smoothing skin comprising applying to skin a skin-tensing and skin-smoothing effective amount of the composition according to claim 1.

34. A method of immediately attenuating wrinkles and/or fine wrinkles comprising applying to skin a wrinkle or fine line attenuating effective amount of the composition of claim 2.

35. A method for treating wrinkled skin comprising applying to the skin a wrinkle treating effective amount of the composition according to claim 2.

36. A method of tensing and smoothing skin comprising applying to skin a skin-tensing and skin-smoothing effective amount of the composition according to claim 2.

37. A method of immediately attenuating wrinkles and/or fine wrinkles comprising applying to skin a wrinkle or fine line attenuating effective amount of the composition of claim 4.

38. A method for treating wrinkled skin comprising applying to the skin a wrinkle treating effective amount of the composition according to claim 4.

39. A method of tensing and smoothing skin comprising applying to skin a skin-tensing and skin-smoothing effective amount of the composition according to claim 4.

40. A method of immediately attenuating wrinkles and/or fine wrinkles comprising applying to skin a wrinkle or fine line attenuating effective amount of the composition of claim 11.

41. A method for treating wrinkled skin comprising applying to the skin a wrinkle treating effective amount of the composition according to claim 11.

42. A method of tensing and smoothing skin comprising applying to skin a skin-tensing and skin-smoothing effective amount of the composition according to claim 11.

43. A composition having an immediate anti-wrinkle effect comprising in a physiologically acceptable medium, an anti-wrinkle effective amount of at least one mineral filler, with the exclusion of any mixed silicate, wherein the mineral filler is in the form of colloid particles in a dispersion in an aqueous medium and at least 70% of the particles have a diameter in the range of about 0.1 to about 100 nm, wherein the colloid particles are present in the composition in an active material amount ranging from 0.5 to about 15% wt, based on the total weight of the composition, wherein the composition is in the form of a water-in-oil (W/O), an oil-in-water (O/W) or a water-in-oil-in-water (W/O/W) emulsion, and wherein the composition is free from glycerin and propylene glycol.

* * * * *